(12) United States Patent
Whyte et al.

(10) Patent No.: US 11,045,594 B2
(45) Date of Patent: *Jun. 29, 2021

(54) DRESSING WITH ASYMMETRIC ABSORBENT CORE FOR NEGATIVE PRESSURE WOUND THERAPY

(71) Applicant: KCI Licensing, Inc., San Antonio, TX (US)

(72) Inventors: David George Whyte, Dorset (GB); Christopher Brian Locke, Bournemouth (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 675 days.

This patent is subject to a terminal disclaimer.

(21) Appl. No.: 15/713,390

(22) Filed: Sep. 22, 2017

(65) Prior Publication Data
US 2018/0008756 A1    Jan. 11, 2018

Related U.S. Application Data

(62) Division of application No. 14/150,262, filed on Jan. 8, 2014, now Pat. No. 9,795,724.

(Continued)

(51) Int. Cl.
*A61M 1/00* (2006.01)
*A61F 13/00* (2006.01)
*A61F 13/02* (2006.01)

(52) U.S. Cl.
CPC ..... *A61M 1/0088* (2013.01); *A61F 13/00029* (2013.01); *A61F 13/00068* (2013.01);

(Continued)

(58) Field of Classification Search
CPC .............. A61M 1/0088; A61M 1/0096; A61M 1/0023; A61F 13/00029; A61F 13/00068;

(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Japanese Notice of Rejection for Corresponding Application No. 2018155994, dated Jul. 23, 2019.

(Continued)

Primary Examiner — Tatyana Zalukaeva
Assistant Examiner — Heather K Barnwell

(57) ABSTRACT

Systems, methods, and apparatuses for treating a tissue site with reduced pressure are described. The system includes a manifold configured to be placed adjacent the tissue site, and a sealing member configured to be placed over the tissue site and the manifold. The system also includes a reduced-pressure source fluidly coupled to the manifold through the sealing member. The system further includes a pouch having an upstream layer having a first thickness, a downstream layer having a second thickness, and an absorbent member enclosed between the upstream layer and the downstream layer. The second thickness is greater than the first thickness. The upstream layer may have a hydrophilic side adjacent the absorbent member, and the downstream layer may have a hydrophobic side adjacent the absorbent member.

14 Claims, 2 Drawing Sheets

Related U.S. Application Data

(60) Provisional application No. 61/753,368, filed on Jan. 16, 2013.

(52) U.S. Cl.
CPC ........ *A61F 13/022* (2013.01); *A61F 13/0206* (2013.01); *A61M 1/0096* (2014.02); *Y10T 156/10* (2015.01); *Y10T 156/1051* (2015.01)

(58) Field of Classification Search
CPC .............. A61F 13/0216; A61F 13/0206; A61F 13/0209; A61F 13/0213; A61F 13/022; A61F 2013/00314; A61F 2013/00319; A61F 2013/00323; A61F 2013/15422
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Guiles, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,667,665 | A | 5/1987 | Blanco et al. |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,673,981 | B1 | 1/2004 | Strombom et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 9,795,724 | B2* | 10/2017 | Whyte .................. A61F 13/022 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2004/0250969 | A1 | 12/2004 | Luu et al. |
| 2005/0143697 | A1 | 6/2005 | Riesinger |
| 2008/0119802 | A1 | 5/2008 | Riesinger |
| 2008/0306456 | A1 | 12/2008 | Riesinger |
| 2009/0204084 | A1 | 8/2009 | Blott et al. |
| 2009/0293887 | A1* | 12/2009 | Wilkes .............. A61F 13/00029 128/888 |
| 2010/0069863 | A1* | 3/2010 | Olson ................. A61M 1/0088 604/368 |
| 2010/0305490 | A1* | 12/2010 | Coulthard ........... A61F 13/0209 602/43 |
| 2011/0313373 | A1 | 12/2011 | Riesinger |
| 2012/0143157 | A1 | 6/2012 | Riesinger |

(56) References Cited

U.S. PATENT DOCUMENTS

| | | |
|---|---|---|
| 2013/0172843 A1 | 7/2013 | Kurata |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2001000119 A1 | 1/2001 |
| WO | 2009089016 A1 | 7/2009 |
| WO | 2009111655 A2 | 9/2009 |
| WO | 2011152368 A1 | 12/2011 |
| WO | 2014113253 A1 | 7/2014 |

OTHER PUBLICATIONS

Extended European Search Report corresponding to EP16176518.5, dated Oct. 4, 2016.
Australian Examination Report for Corresponding Application No. 2018204175, dated Jan. 28, 2019.
Chinese Second Office Action for Corresponding Application No. 2014800041315, dated Dec. 3, 2018.
Chinese First Office Action for corresponding Application No. 2014800041315, dated Mar. 19, 2018.
Japanese Notice of Rejection corresponding to Application No. 2015552746, dated Nov. 14, 2017.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Egnell Minor: Addition to the Users Manual Concerning Overflow Protection—Concerns all Egnell Pumps, Feb. 3, 1983, pp. 2.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
International Search Report for PCT International Application PCT/GB95/01983; dated Nov. 23, 1995.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (and certified translation).

F.E. Johnson, "An Improved Technique for Skin Graft Placement Using a Suction Drain," Surgery, Gynecology, and Obstetrics 159 (1984), pp. 584-585.

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

DRESSING WITH ASYMMETRIC ABSORBENT CORE FOR NEGATIVE PRESSURE WOUND THERAPY

RELATED APPLICATIONS

This application is a divisional of U.S. patent application Ser. No. 14/150,262, filed Jan. 8, 2014, which claims the benefit, under 35 USC 119(e), of the filing of U.S. Provisional Patent Application No. 61/753,368, entitled "Dressing with Asymmetric Absorbent Core for Negative Pressure Wound Therapy," filed Jan. 16, 2013, which is incorporated herein by reference for all purposes.

TECHNICAL FIELD

The present disclosure relates generally to medical treatment systems for treating tissue sites and processing fluids. More particularly, but not by way of limitation, the present disclosure relates to a dressing having an asymmetric absorbent core for reduced-pressure wound therapy.

BACKGROUND

Clinical studies and practice have shown that reducing pressure in proximity to a tissue site can augment and accelerate growth of new tissue at the tissue site. The applications of this phenomenon are numerous, but is has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients. In particular, reduced-pressure dressings that include an absorbent member positioned proximate a tissue site may experience absorbent material loss or inefficient absorption that negatively impacts the ability of a reduced-pressure system to provide reduced-pressure therapy to a tissue site.

SUMMARY

According to an illustrative embodiment, a system for collecting fluid from a tissue site is described. The system may include a manifold adapted to be placed adjacent the tissue site, a sealing member adapted to be placed over the tissue site and a reduced-pressure source adapted to be fluidly coupled to the manifold through the sealing member. The system further may include a pouch. The pouch may include an upstream layer having a first thickness, a hydrophilic side, and a hydrophobic side, and a downstream layer having a second thickness, a hydrophilic side, and a hydrophobic side. The apparatus also may include an absorbent member enclosed between the upstream layer and the downstream layer. The hydrophilic side of the upstream layer may be positioned adjacent the absorbent member so that the hydrophobic side of the upstream layer forms a portion of an exterior of the apparatus. The hydrophobic side of the downstream layer may be positioned adjacent the absorbent member so that the hydrophilic side of the downstream layer forms another portion of the exterior of the apparatus. The second thickness may be greater than the first thickness.

According to another illustrative embodiment, a system for treating a tissue site with reduced pressure is described. The system may include a manifold adapted to be placed adjacent the tissue site, a sealing member adapted to be placed over the tissue site and the manifold to provide a substantially air-tight seal at the tissue site, and a reduced-pressure source adapted to be fluidly coupled to the manifold through the sealing member. The system further may include a pouch. The pouch may include an upstream layer having a hydrophilic side and a hydrophobic side, a downstream layer having a hydrophilic side and a hydrophobic side, and an absorbent member enclosed between the upstream layer and the downstream layer. The hydrophilic side of the upstream layer may be positioned adjacent the absorbent member, and the hydrophobic side of the downstream layer may be positioned adjacent the absorbent member. The pouch may be adapted to be positioned between the manifold and the sealing member.

According to yet another illustrative embodiment, an apparatus for collecting fluid from a tissue site is described. The apparatus may include an upstream layer having a hydrophilic side and a hydrophobic side, and a downstream layer having a hydrophilic side and a hydrophobic side. The apparatus also may include an absorbent member enclosed between the upstream layer and the downstream layer. The hydrophilic side of the upstream layer may be positioned adjacent the absorbent member so that the hydrophobic side of the upstream layer forms a portion of an exterior of the apparatus. The hydrophobic side of the downstream layer may be positioned adjacent the absorbent member so that the hydrophilic side of the downstream layer forms another portion of the exterior of the apparatus.

According to still another illustrative embodiment, a system for treating a tissue site with reduced pressure is described. The system may include a manifold adapted to be placed adjacent the tissue site, a sealing member adapted to be placed over the tissue site and the manifold to provide a substantially air-tight seal at the tissue site, and a reduced-pressure source adapted to be fluidly coupled to the manifold through the sealing member. The system further may include a pouch. The pouch may have an upstream layer having a first thickness, a downstream layer having a second thickness, and an absorbent member enclosed between the upstream layer and the downstream layer. The second thickness may be greater than the first thickness, and the pouch may be adapted to be positioned between the manifold and the sealing member.

According to still another illustrative embodiment, an apparatus for collecting fluid from a tissue site is described. The apparatus may include a pouch. The pouch may have an upstream layer having a first thickness, a downstream layer having a second thickness, and an absorbent member enclosed between the upstream layer and the downstream layer. The second thickness may be greater than the first thickness, and the pouch may be adapted to be positioned between the manifold and the sealing member.

According to yet another illustrative embodiment, a method for treating a tissue site is described. The method positions a manifold adjacent the tissue site and provides a pouch. The pouch may include an upstream layer having a hydrophilic side and a hydrophobic side, a downstream layer having a hydrophilic side and a hydrophobic side, and an absorbent member enclosed between the upstream layer and the downstream layer. The hydrophilic side of the upstream layer may be positioned adjacent the absorbent member so that the hydrophobic side of the upstream layer forms a portion of an exterior of the apparatus. The hydrophobic side of the downstream layer may be positioned adjacent the absorbent member so that the hydrophilic side of the downstream layer forms another portion of the exterior of the apparatus. The method may position the pouch adjacent the manifold and the tissue site so that the upstream layer is adjacent the manifold. The pouch may include an upstream layer having a first thickness, a downstream layer having a second thickness greater than the first thickness, and an absorbent member having absorbent material disposed between the upstream layer and the downstream layer so that the upstream layer and the downstream layer enclose the absorbent member. The method may position a sealing member over the manifold and the pouch to provide a substantially air-tight seal and fluidly couples a reduced-pressure source to the manifold to provide reduced pressure to the tissue site. The method may distribute reduced pressure to the manifold through the pouch and distributes fluid from the tissue site to an absorbent member in the pouch for storage therein.

According to another illustrative embodiment, a method for manufacturing a fluid storage canister is described. The method provides a first layer having a first thickness, a hydrophilic side, and a hydrophobic side. The method positions an absorbent member adjacent the hydrophilic side of the first layer. The method also provides a second layer have a second thickness greater than the first thickness, a hydrophilic side and a hydrophobic side. The method positions the hydrophilic side of the second layer adjacent the absorbent member. The method couples peripheral portions of the first layer and the second layer to each other to enclose the absorbent member.

Other aspects, features, and advantages of the illustrative embodiments will become apparent with reference to the drawings and detailed description that follow.

DETAILED DESCRIPTION OF ILLUSTRATIVE EMBODIMENTS

New and useful systems, methods, and apparatuses for fluid storage in a reduced-pressure therapy environment are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative exemplary embodiments, variations, and equivalents not specifically described in detail. The following detailed description should therefore be taken as illustrative and not limiting.

The exemplary embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
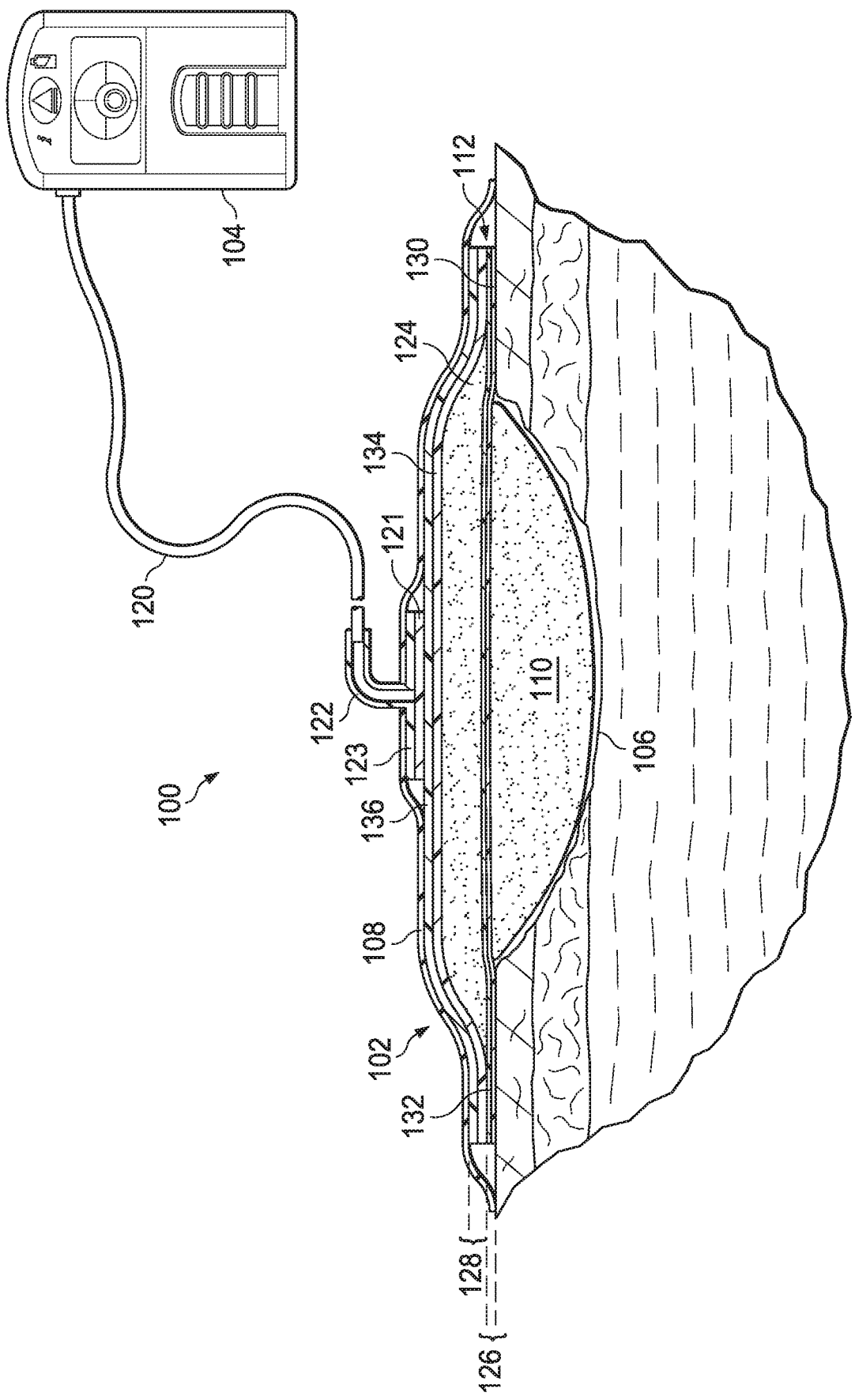
FIG. 1 is sectional view illustrating a reduced-pressure therapy system in accordance with an exemplary embodiment.

FIG. 1 is a sectional view of an exemplary embodiment illustrating a therapy system 100 for supplying reduced pressure to a tissue site 106. The therapy system 100 may include a dressing 102 in fluid communication with the tissue site 106, a reduced-pressure source 104 for providing reduced pressure to a tube 120 that may be fluidly coupled to the reduced-pressure source 104, and a connector 122 that may fluidly couple the tube 120 to the dressing 102.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A tissue site may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

A reduced-pressure source, such as the reduced-pressure source 104, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation may be generally presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications (such as by substituting a positive-pressure source for a reduced-pressure source) and this descriptive convention should not be construed as a limiting convention.

"Reduced pressure" generally refers to a pressure less than a local ambient pressure, such as the ambient pressure in a local environment external to a sealed therapeutic environment. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The components of the therapy system 100 may be coupled directly or indirectly. Components may be fluidly coupled to each other to provide a path for transferring fluids (for example, liquid and/or gas) between the components. In some exemplary embodiments, components may be fluidly coupled with a conduit, such as the tube 120, for example. A "tube," as used herein, broadly refers to a tube, pipe, hose, conduit, or other structure with one or more lumina adapted to convey fluids between two ends. Typically, a tube may be an elongated, cylindrical structure with some flexibility, but the geometry and rigidity may vary. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The reduced pressure developed by the reduced-pressure source 104 may be delivered through the tube 120 to the connector 122. The connector 122 may be a device configured to fluidly couple the reduced-pressure source 104 to the dressing 102. In some exemplary embodiments, the connector 122 may include a flange portion 123 that may couple to the dressing 102 and a port portion that may fluidly couple to the tube 120. The port portion may be fluidly sealed to the flange portion 123 and may provide fluid communication through the flange portion 123. In some embodiments, the connector 122 may prevent fluid communication between a sealed therapeutic environment formed by the dressing 102 and the ambient environment. The connector 122 may allow fluid communication through the dressing 102 between the tissue site 106 and the tube 120. The connector 122 may also include a primary filter 121 disposed within a fluid channel of the connector 122. The primary filter 121 may be a hydrophobic material substantially filling the fluid channel through the connector 122 and adapted to limit passage of liquids through the connector 122 into the tube 120. In some embodiments, the connector 122 may be a T.R.A.C.® Pad or Sensa T.R.A.C.® Pad available from Kinetic Concepts, Inc. (KCI) of San Antonio, Tex. In other exemplary embodiments, the connector 122 may be a conduit inserted into the dressing 102.

The dressing 102 may include a manifold 110 adapted to be in fluid communication with the tissue site 106, a pouch 112 adapted to be in fluid communication between the manifold 110 and the connector 122, and a drape 108 covering both the manifold 110 and the pouch 112 at the tissue site 106. The manifold 110 may be placed within, over, on, or otherwise proximate a tissue site, for example, the tissue site 106. The pouch 112 may be placed adjacent the manifold 110, and the drape 108 may be placed over the manifold 110 and sealed to tissue proximate the tissue site 106. The tissue proximate the tissue site 106 may often be undamaged epidermis peripheral to the tissue site 106. Thus, the dressing 102 can provide the sealed therapeutic environment proximate the tissue site 106, substantially isolating the tissue site 106 from the external environment. The reduced-pressure source 104 can reduce the pressure in the sealed therapeutic environment. Reduced pressure applied uniformly through the manifold 110 in the sealed therapeutic environment can induce macrostrain and microstrain in the tissue site 106, as well as remove exudates and other fluids from the tissue site 106, which can be collected in the pouch 112 and disposed of properly.

In some embodiments, the manifold 110 contacts the tissue site 106. The manifold may be partially or fully in contact with the tissue site 106. If the tissue site 106 extends into tissue from a tissue surface, for example, the manifold 110 may partially or completely fill the tissue site 106. In other exemplary embodiments, the manifold 110 may be placed over the tissue site 106. The manifold 110 may take many forms, and may have many sizes, shapes, or thicknesses depending on a variety of factors, such as the type of treatment being implemented or the nature and size of the tissue site 106. For example, the size and shape of the manifold 110 may be adapted to the contours of deep and irregular shaped tissue sites.

The manifold 110 may be a substance or structure adapted to distribute reduced pressure to a tissue site, remove fluids from a tissue site, or distribute reduced pressure to and remove fluids from a tissue site. In some exemplary embodiments, a manifold may also facilitate delivering fluids to a tissue site, for example, if the fluid path is reversed or a secondary fluid path is provided. A manifold may include flow channels or pathways that distribute fluids provided to and removed from a tissue site around the manifold. In one exemplary embodiment, the flow channels or pathways may be interconnected to improve distribution of fluids provided to or removed from a tissue site. For example, cellular foam, open-cell foam, porous tissue collections, and other porous material, such as gauze or felted mat, generally include structural elements arranged to form flow channels. Liquids, gels, and other foams may also include or be cured to include flow channels.

In one exemplary embodiment, the manifold 110 may be a porous foam material having interconnected cells or pores adapted to uniformly (or quasi-uniformly) distribute reduced pressure to the tissue site 106. The foam material may be either hydrophobic or hydrophilic. In one non-limiting example, the manifold 110 can be an open-cell, reticulated polyurethane foam such as GranuFoam® dressing available from Kinetic Concepts, Inc. of San Antonio, Tex.

In an example in which the manifold 110 may be made from a hydrophilic material, the manifold 110 may also wick fluid away from the tissue site 106, while continuing to distribute reduced pressure to the tissue site 106. The wicking properties of the manifold 110 may draw fluid away from the tissue site 106 by capillary flow or other wicking mechanisms. An example of a hydrophilic foam may be a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 110 may further promote granulation at the tissue site 106 if pressure within the sealed therapeutic environment is reduced. For example, any or all of the surfaces of the manifold 110 may have an uneven, coarse, or jagged profile that can induce microstrains and stresses at the tissue site 106 if reduced pressure is applied through the manifold 110 to the tissue site 106.

In one exemplary embodiment, the manifold 110 may be constructed from bioresorable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 110 may further serve as a scaffold for new cell-growth, or a scaffold material may be used in conjunction with the manifold 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 may include a sealing member. A sealing member may be constructed from a material that can provide a fluid seal between two components or two environments, such as between the sealed therapeutic environment and a local ambient environment. A sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. The drape 108 may further include an attachment device that may be used to attach the sealing member to an attachment surface, such as undamaged epidermis, a gasket, or another sealing member. The attachment device may take many forms. For example, an attachment device may be a medically acceptable, pressure-sensitive adhesive that extends about a periphery of, a portion of, or an entirety of the sealing member. Other exemplary embodiments of an attachment device may include a double-sided tape, paste, hydrocolloid, hydrogel, silicone gel, organogel, or an acrylic adhesive.

Figure 2:
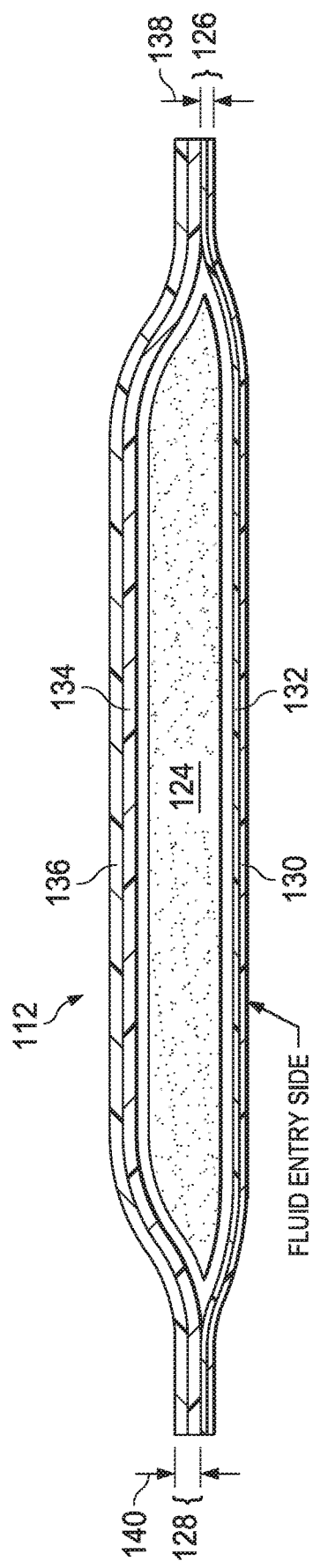
FIG. 2 is a sectional view illustrating a pouch of the reduced-pressure therapy system of FIG. 1.

Referring more specifically to FIG. 2, the pouch 112 may include an absorbent member 124, a first outer layer, such as an upstream layer 126, and a second outer layer, such as a downstream layer 128. The upstream layer 126 and the downstream layer 128 envelop or enclose the absorbent member 124, which absorbs bodily fluids drawn by the reduced pressure through the upstream layer 126.

The absorbent member 124 may be formed of or include an absorbent material. The absorbent material functions to hold, stabilize, and/or solidify fluids that may be collected from the tissue site 106. The absorbent material may be of the type referred to as "hydrogels," "super-absorbents," or "hydrocolloids." If disposed within the dressing 102, the absorbent material may be formed into fibers or spheres to manifold reduced pressure until the absorbent member 124 becomes saturated. Spaces or voids between the fibers or spheres may allow a reduced pressure that is supplied to the dressing 102 to be transferred within and through the absorbent member 124 to the manifold 110 and the tissue site 106. In some exemplary embodiments, the absorbent material may be Texsus FP2325 having a material density of 800 grams per square meter (gsm). In other exemplary embodiments, the absorbent material may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the absorbent material may be formed of granular absorbent components that may be scatter coated onto a paper substrate. Scatter coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material. The absorbent materials that may be formed using a scatter coating process experience partial absorbent material loss during handling. The absorbent material loss may occur while positioning the absorbent material proximate the tissue site, while transporting the absorbent material from the manufacturing facility to the facility of use, or during the process of manufacturing a pouch formed solely of absorbent material.

In some exemplary embodiments, the upstream layer 126 and the downstream layer 128 have perimeter dimensions that may be larger than the perimeter dimensions of the absorbent member 124 so that, if the absorbent member 124 is positioned between the upstream layer 126 and the downstream layer 128 and the center portions of the absorbent member 124, the upstream layer 126, and the downstream layer 128 are aligned, the upstream layer 126 and the downstream layer 128 may extend beyond the perimeter of the absorbent member 124. In some exemplary embodiments, the upstream layer 126 and the downstream layer 128 surround the absorbent member 124. Peripheral portions of the upstream layer 126 and the downstream layer 128 may be coupled so that the upstream layer 126 and the downstream layer 128 enclose the absorbent member 124. The upstream layer 126 and the downstream layer 128 may be coupled by high frequency welding, ultrasonic welding, heat welding, or impulse welding, for example. In other exemplary embodiments, the upstream layer 126 and the downstream layer 128 may be coupled by bonding or folding, for example.

Figure 3:
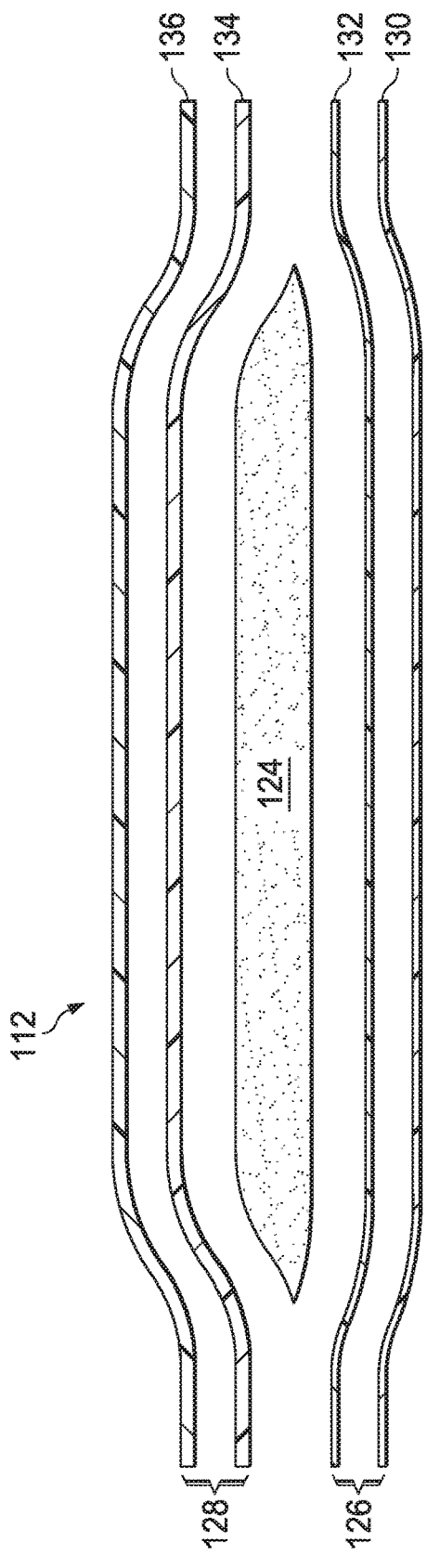
FIG. 3 is an exploded sectional view of the pouch of FIG. 2.

Referring more specifically to FIG. 2 and FIG. 3, the upstream layer 126 may have a first side, such as a hydrophobic side 130, and a second side, such as a hydrophilic side 132. The hydrophilic side 132 may be positioned adjacent the absorbent member 124 such that the hydrophobic side 130 of the upstream layer 126 is also an upstream side of the pouch 112. The upstream layer 126 may be formed of non-woven material having a thickness 138. In some exemplary embodiments, the upstream layer 126 may have a polyester fibrous porous structure. The upstream layer 126 may be porous, but preferably not be perforated. The upstream layer 126 may have a material density of about 80 gsm. In other exemplary embodiments, the material density may be lower or greater depending on the particular application of the pouch 112. The upstream layer 126 may be formed of Libeltex TDL2, for example.

The hydrophobic side 130 may be configured to distribute bodily fluids from the manifold 110 across the upstream surface area of the pouch 112. The hydrophobic side 130 may also be referred to as a wicking side, wicking surface, distribution surface, distribution side, or fluid distribution surface. The hydrophobic side 130 may be a smooth distribution surface configured to move fluid through the upstream layer 126 along a grain of the upstream layer 126, distributing fluid throughout the upstream layer 126. The hydrophilic side 132 may be configured to acquire bodily fluid from the hydrophobic side 130 to aid in bodily fluid movement into the absorbent member 124. The hydrophilic side 132 may also be referred to as a fluid acquisition surface, fluid acquisition side, hydrophilic acquisition surface, or hydrophilic acquisition side. The hydrophilic side 132 may be a fibrous surface and be configured to draw fluid into the upstream layer 126. While illustrated in FIG. 3 as separate components, the hydrophilic side 132 and the hydrophobic side 130 of the upstream layer 126 may be opposite sides of the upstream layer 126 and are shown as separate components to aid in explanation.

The downstream layer 128 may have a first side, such as a hydrophobic side 134, and a second side, such as a hydrophilic side 136. The hydrophobic side 134 may be positioned adjacent the absorbent member 124 so that the hydrophilic side 136 of the downstream layer 128 is also a downstream side of the pouch 112. The downstream layer 128 may be formed of a non-woven material having a thickness 140. In some exemplary embodiments, the downstream layer 128 may have a polyester fibrous porous structure. The downstream layer 128 may be porous, but preferably not be perforated. The downstream layer 128 may have a material density of about 150 gsm. In other exemplary embodiments, the material density may be lower or greater depending on the particular application of the pouch 112. The material density of the downstream layer 128 may be greater than the material density of the upstream layer 126. The thickness 140 of the downstream layer 128 may be greater than the thickness 138 of the upstream layer 126. In the exemplary embodiment illustrated in FIGS. 2 and 3, the thickness 140 may be about three times greater than the thickness 138. The downstream layer 128 may be formed of Libeltex TL4. In other exemplary embodiments, the downstream layer 128 may be formed of Libeltex TDL2.

The hydrophobic side 134 may be disposed adjacent the absorbent member 124 on an opposite side of the absorbent member 124 from the hydrophilic side 132 of the upstream layer 126. The hydrophobic side 134 may be configured to distribute bodily fluids not contained by the absorbent member 124 to the hydrophilic side 136 of the downstream layer 128. The hydrophobic side 134 may also be referred to as a wicking side, wicking surface, distribution surface, distribution side, or fluid distribution surface. The hydrophobic side 134 may be a smooth distribution surface configured to move fluid through the downstream layer 128 along a grain of the downstream layer 128, distributing fluid throughout downstream layer 128. The hydrophilic side 136 may be configured to acquire excess bodily fluids wicked by the hydrophobic side 134 from the absorbent member 124. The hydrophilic side 136 may also be referred to as a fluid acquisition surface, fluid acquisition side, hydrophilic acquisition surface, or hydrophilic acquisition side. The hydrophilic side 136 may be a fibrous surface and be configured to draw fluid into the downstream layer 128. While illustrated in FIG. 3 as separate components, the hydrophobic side 134 and the hydrophilic side 136 may be opposite sides of the downstream layer 128 and may be shown as separate components to aid in explanation of the described exemplary embodiments.

As described herein, the upstream layer 126 and the downstream layer 128 contain the absorbent member 124, reducing absorbent material loss during manufacturing, shipping, and use of the pouch 112. Containment of the absorbent material prevents loss of the granular absorbent components as the pouch 112 may be moved during the manufacturing process. In addition, containment of the absorbent material in the pouch 112 formed from the upstream layer 126 and the downstream layer 128 may reduce loss of the granular absorbent components during use of the pouch 112, for example, while placing the pouch 112 adjacent the tissue site 106 or positioning the pouch 112 in the therapy system 100. Still further, if the pouch 112 is used at the tissue site 106, containment of the absorbent material may limit migration of the granular absorbent components into the tissue site 106.

If the tissue site 106 is small, the pouch 112 may aid the manifold 110 in distribution of reduced pressure to the tissue site 106. The upstream layer 126 and the downstream layer 128 may enclose the absorbent member 124, manifold reduced pressure to the tissue site 106, and wick fluids from the tissue site 106 into the absorbent member 124. The pouch 112 may accommodate the increased difficulties of enclosing, manifolding, and wicking that may be experienced when treating a smaller tissue site 106. In addition, the pouch 112 may prevent the loss of structural integrity associated with using scatter coated absorbent material to form the absorbent member 124 that may often lead to more frequent replacement of the pouch 112.

During the application of reduced pressure, some pouches containing absorbent materials tend to become saturated at the point of fluid entry into the absorbent member itself. If the absorbent material becomes saturated in one area prior to saturation of the absorbent material in other areas, the absorbent material experiences a reduced ability to move fluid from the point of entry to areas of the absorbent material that may be unsaturated. In addition, the amount of reduced pressure distributed to the tissue site may be reduced, decreasing the therapeutic benefits of using reduced pressure. If pouches are decreased in size to be placed adjacent smaller tissue sites or tissue sites that produce smaller amounts of exudate, the pouch's absorbent capability may be further reduced. If the absorbent capability of such pouches is reduced, more frequent dressing changes may be needed, thereby increasing the cost of supplying reduced-pressure therapy.

As disclosed herein, the therapy system 100 overcomes these shortcomings and others by providing the pouch 112 as described above with respect to FIGS. 2-3. In the operative exemplary embodiments, the rate of fluid flow received by the pouch 112 may be relatively slow for a relatively long duration. Placing the hydrophobic side 130 of the upstream layer 126 adjacent the manifold 110 may allow the hydrophobic nature of the hydrophobic side 130 to move the fluid along a grain (not shown) of the hydrophobic side 130 across a width of the upstream layer 126. The fluid movement may be parallel to the manifold 110 and away from the strongest point of reduced pressure. This wicking action spreads the fluid drawn from the tissue site 106 across a wider area. As the fluid moves through the upstream layer 126 from the hydrophobic side 130 toward the absorbent member 124 it reaches the hydrophilic side 132. The hydrophilic side 132 draws the fluid into the absorbent member 124. The gradient of hydrophilicity increases from the hydrophobic side 130 to the hydrophilic side 132 as the fluid moves downstream toward the absorbent member 124.

In operation, the increased thickness 140 and increased material density of the downstream layer 128 aid the distribution of reduced pressure to the upstream layer 126 and the manifold 110. In one exemplary embodiment, the upstream layer 126 may have a density of about 80 gsm, and the downstream layer 128 may have a density of about 150 gsm so that the relative thickness of the downstream layer 128 to the upstream layer 126 may be about 1.875. The relative thickness of the downstream layer 128 in other exemplary embodiments may fall in the range from about 1.5 to about 3.0 for other reduced-pressure therapy applications. The distribution of reduced pressure by the downstream layer 128 aids the wicking action of the hydrophobic side 130 of the upstream layer 126 so that fluids drawn from the tissue site 106 may be more evenly distributed in the dressing 102. In turn, more even distribution of the fluids drawn from the tissue site 106 provides for more efficient use of the absorbent member 124, increasing the time between replacement of the dressing 102, and decreasing costs as fewer dressings may be needed to absorb an equivalent amount of fluid.

Positioning of the upstream layer 126 and the downstream layer 128, as described herein, may orient grains of the upstream layer 126 and the downstream layer 128 in a manner that increases the efficient use of the absorbent member 124. By placing the hydrophilic side 136 proximate the reduced-pressure source 104. The hydrophilic side 136 may also act as an additional filter mechanism that may aid in preventing blockage of the primary filter 121 of the connector 122. The duration during which the dressing 102 can manifold reduced pressure may also extended. By using materials that provide a wicking function, the efficient use of available absorbent materials can be improved.

The use of layers that wick fluids and manifold reduced pressure allows for controlled use of the available absorbent material. The layers, arranged as described above, distribute reduced pressure such that fluid may be more evenly distributed to the absorbent member of the pouch, increasing the total time necessary to saturate the absorbent materials of the absorbent member as more fluid pathways may be used to distribute the fluid. The use of layers to form the pouch with structures of differing hydrophilicity allows for better control of the fluids entering the absorbent member of the pouch. The use of layers having different coatweights allows the properties of the pouch to be matched to the application in a technically better and cost effective solution. The solution disclosed will result in a greater level of absorption before capacity may be reached without requiring additional absorbent material.

The systems and methods described herein may provide significant advantages, some of which have already been mentioned. For example, the therapy system provides improved materials efficiency, lower cost, and does a better job at manifolding reduced pressure. The disclosed exemplary embodiment may also be used with inline canisters, for example, fluid absorbing pouches or fluid absorbing canisters disposed external to the dressing.

It should be apparent from the foregoing that an invention having significant advantages has been provided. While shown in only a few forms, the systems and methods illustrated are susceptible to various changes and modifications without departing from the spirit thereof.

Although certain illustrative, non-limiting exemplary embodiments have been presented, it should be understood that various changes, substitutions, permutations, and alterations can be made without departing from the scope the appended claims. It will be appreciated that any feature that is described in connection to any one exemplary embodiment may also be applicable to any other exemplary embodiment.

It will be understood that the benefits and advantages described above may relate to one exemplary embodiment or may relate to several exemplary embodiments. It will further be understood that reference to "an" item refers to one or more of those items.

The steps of the methods described herein may be carried out in any suitable order, or simultaneously where appropriate.

Where appropriate, features of any of the exemplary embodiments described above may be combined with features of any of the other exemplary embodiments described to form further examples having comparable or different properties and addressing the same or different problems.

It will be understood that the above description of preferred exemplary embodiments is given by way of example only and that various modifications may be made by those skilled in the art. The above specification, examples and data provide a complete description of the structure and use of exemplary embodiments of the invention. Although various exemplary embodiments of the invention have been described above with a certain degree of particularity, or with reference to one or more individual exemplary embodiments, those skilled in the art could make numerous alterations to the disclosed exemplary embodiments without departing from the scope of the claims.

We claim:

1. A system for treating a tissue site with reduced pressure, the system comprising:
    a manifold adapted to be placed adjacent the tissue site;
    a sealing member adapted to be placed over the tissue site and the manifold to provide a seal at the tissue site;
    a reduced-pressure source adapted to be fluidly coupled to the manifold through the sealing member; and
    a pouch adapted to be positioned between the manifold and the sealing member, the pouch comprising:
        an upstream layer having a hydrophilic side and a hydrophobic side,
        a downstream layer having a hydrophilic side and a hydrophobic side, wherein peripheral portions of the upstream layer and the downstream layer are configured to be coupled, and
        an absorbent member enclosed between the upstream layer and the downstream layer, the hydrophilic side of the upstream layer positioned adjacent the absorbent member and the hydrophobic side of the downstream layer positioned adjacent the absorbent member.

2. The system of claim 1, wherein the upstream layer has a first thickness and the downstream layer has a second thickness, and the second thickness is greater than the first thickness.

3. The system of claim 1, wherein the upstream layer has a first thickness and the downstream layer has a second thickness, and the second thickness is about three times greater than the first thickness.

4. The system of claim 1, wherein the upstream layer has a material density of about 80 gsm.

5. The system of claim 1, wherein the downstream layer has a material density of about 150 gsm.

6. The system of claim 1, wherein the upstream layer has a material density of about 80 gsm and the downstream layer has a material density of about 150 gsm.

7. The system of claim 1, wherein:
wherein the upstream layer has a first thickness and the downstream layer has a second thickness;
the second thickness is about three times greater than the first thickness;
the upstream layer has a material density of about 80 gsm; and
the downstream layer has a material density of about 150 gsm.

8. An apparatus for collecting fluid from a tissue site, the apparatus comprising:
an upstream layer having a hydrophilic side and a hydrophobic side;
a downstream layer having a hydrophilic side and a hydrophobic side, wherein peripheral portions of the upstream layer and the downstream layer are configured to be coupled; and
an absorbent member enclosed between the upstream layer and the downstream layer, the hydrophilic side of the upstream layer positioned adjacent the absorbent member so that the hydrophobic side of the upstream layer forms a portion of an exterior of the apparatus, and the hydrophobic side of the downstream layer positioned adjacent the absorbent member so that the hydrophilic side of the downstream layer forms another portion of the exterior of the apparatus.

9. The apparatus of claim 8, wherein the upstream layer has a first thickness and the downstream layer has a second thickness, and the second thickness is greater than the first thickness.

10. The apparatus of claim 8, wherein the upstream layer has a first thickness and the downstream layer has a second thickness, and the second thickness is about three times greater than the first thickness.

11. The apparatus of claim 8, wherein the upstream layer has a material density of about 80 gsm.

12. The apparatus of claim 8, wherein the downstream layer has a material density of about 150 gsm.

13. The apparatus of claim 8, wherein the upstream layer has a material density of about 80 gsm and the downstream layer has a material density of about 150 gsm.

14. The apparatus of claim 8, wherein:
wherein the upstream layer has a first thickness and the downstream layer has a second thickness;
the second thickness is about three times greater than the first thickness;
the upstream layer has a material density of about 80 gsm; and
the downstream layer has a material density of about 150 gsm.

* * * * *